United States Patent [19]

Thompson

[11] 4,266,188

[45] May 5, 1981

[54] METHOD AND APPARATUS FOR MEASURING A COMPONENT IN A FLOW STREAM

[75] Inventor: Francis Thompson, Plano, Tex.

[73] Assignee: Mobil Oil Corporation, New York, N.Y.

[21] Appl. No.: 99,239

[22] Filed: Nov. 30, 1979

[51] Int. Cl.³ .......................................... G01R 27/02
[52] U.S. Cl. .............................. 324/65 R; 73/61.1 R; 324/61 R
[58] Field of Search ................ 324/65 R, 65 P, 61 R, 324/61 P, 57 R; 73/19, 23, 29, 61.1 R

[56] References Cited

U.S. PATENT DOCUMENTS

| | | | |
|---|---|---|---|
| 2,751,777 | 6/1956 | Cherrier | 324/65 P |
| 2,845,790 | 8/1958 | Eddy | 324/65 P |
| 2,882,212 | 4/1959 | Beard | 73/23 X |
| 3,246,145 | 4/1966 | Higgins . | |
| 3,246,180 | 4/1966 | Keeney, Jr. . | |
| 3,287,960 | 11/1966 | Abercrombie, Jr. . | |
| 3,359,787 | 12/1967 | Zemanek, Jr. . | |
| 3,385,108 | 5/1968 | Rosso . | |
| 3,438,241 | 4/1969 | McKinley, Jr. | 73/19 |
| 3,500,187 | 3/1970 | Fegan, Jr. | 324/65 R |
| 3,504,664 | 4/1970 | Haddad | 324/65 R X |
| 3,580,072 | 5/1971 | Cox . | |
| 3,693,435 | 9/1972 | Cox et al. . | |
| 4,112,744 | 9/1978 | Tassano . | |
| 4,131,773 | 12/1978 | Maham et al. | 73/61.1 R X |

Primary Examiner—Stanley T. Krawczewicz
Attorney, Agent, or Firm—C. A. Huggett; M. G. Gilman; F. J. Kowalski

[57] ABSTRACT

A method and apparatus for measuring the concentration of a particular component, e.g. water, in a two-component mixture, e.g. water-oil. A probe having three sets of sensor electrodes is positioned into the mixture. A first elastic sac is secured over the exposed ends of a first set of electrodes and is filled with water. A second elastic sac is secured over the exposed ends of a second set of electrodes and is filled with oil. The ends of the third set of electrodes are left exposed. The electrodes are energized and each generate a signal representative of a measured electrical property, e.g. resistivity, conductivity, or capacitance, of the liquid in which they are immersed. By properly combining these three signals, the concentration of the particular component is determined. Since any changes in temperature and pressure in the mixture being measured with affect the readings from all three sensors equally, the probe is considered self-adjusting and the accuracy of the final measurement is relatively unaffected by these changes.

18 Claims, 4 Drawing Figures

U.S. Patent  May 5, 1981  4,266,188
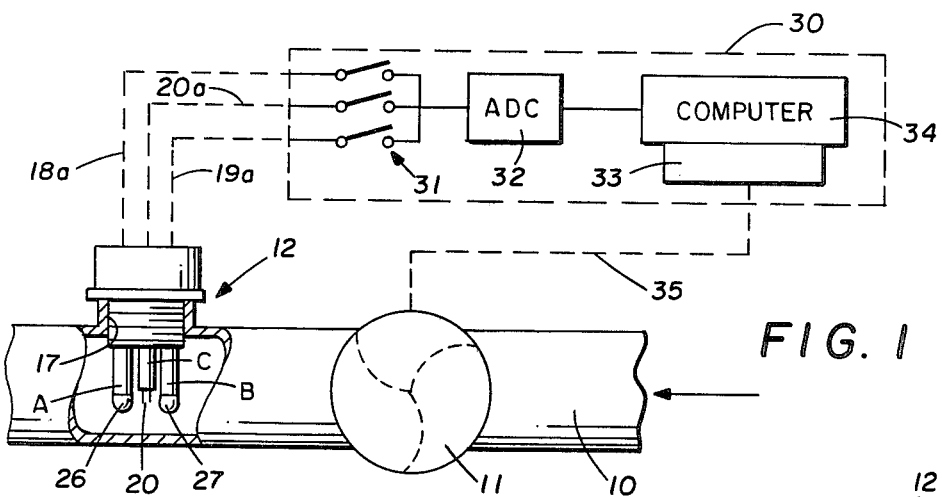
FIG. 1
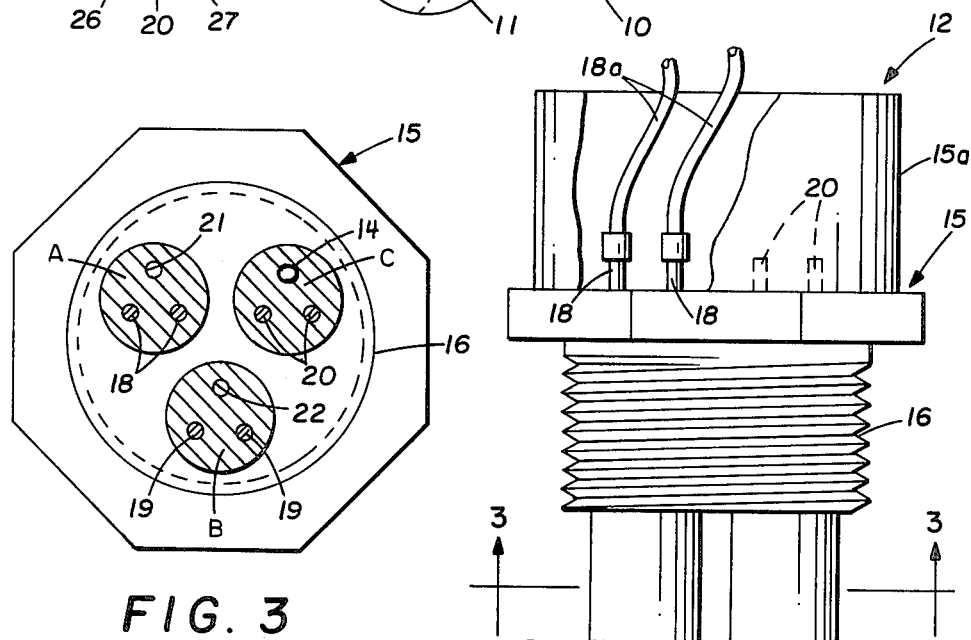
FIG. 3
FIG. 4
FIG. 2

METHOD AND APPARATUS FOR MEASURING A COMPONENT IN A FLOW STREAM

BACKGROUND OF THE INVENTION

The present invention relates to measuring fluid composition and more particularly relates to a method and apparatus for measuring the concentration of a particular component in a two-component liquid flow stream.

There are many situations where it is necessary to determine the amount of a contaminant in a liquid stream. For example, in the oil industry, crude oil that is delivered through a gathering system to a pipeline or other terminal point normally is monitored with regard to its water content. This is routinely accomplished by means of a device commonly termed a "BS&W" or "water-cut" monitor which measures the concentration of water in the crude oil as the crude oil flows through a conduit. The water-cut monitors in most common use today are of the capacitance-probe type. The probe is inserted into the conduit and detects the presence of water by means of a change in the dielectric constant of the oil stream as it flows through the conduit and contacts the electrodes of the probe. This type monitor produces a read-out signal which is indicative of the percent water-cut, i.e. the concentration of water (and therefor of oil) in the crude oil stream at the instance that the measurement is made. Since the dielectric constants of most petroleum oils are in the nature of about 40 times as great as the dielectric constant of water, relatively small amounts of water may be detected by this type of monitor.

Available water-cut monitors of the type described above normally provide measurements of high accuracy and reliability when properly calibrated and operated under stable conditions. However, they are relatively expensive to use due to the sophisticated electronics involved. Also, they normally require a high caliber of preventive maintenance which may not always be convenient. Still more importantly, the readings of capacitance generated by presently known capacitance-type probes are directly related to the temperature and pressure of the liquid stream being monitored. This requires a particular capacitance-type probe to be recalibrated before almost every use to establish proper reference values, at the particular temperature and pressure expected to be encountered during the monitoring operation. Once calibrated for a particular temperature and pressure, a probe of this type will normally provide acceptable readings when minor temperature and pressure changes occur in the flow stream during a monitoring operation but is unable to maintain acceptable accuracy when major changes in temperature and pressure occur.

SUMMARY OF THE INVENTION

The present invention provides a method and apparatus for measuring the concentration, i.e. percentage of a particular component (e.g. water) in a two-component (e.g. oil-water) liquid flow stream wherein the accuracy of the measurement is substantially unaffected by changes in the temperature and/or pressure of the monitored flow stream. A probe which automatically compensates for any changes in temperature and/or pressure of the flow stream during monitoring is used to measure an electrical property, (e.g. resistivity, conductivity, or capacitance) of the flow stream which is then processed to provide the concentrations of the components of the flow stream.

More specifically, in carrying out the method of the present invention, a probe is positioned into the flow stream to be monitored. The probe is comprised of a housing having three individual sets of electrodes thereon. A ballon-like, elastic sac is positioned over the exposed, lower ends of a first set of electrodes to enclose the electrodes in a fluid-tight relationship. This sac is filled with 100% pure component to be measured, e.g. water. A second ballon-like, elastic sac is positioned over the exposed, lower ends of a second set of the electrodes to enclose the electrodes in a fluid-tight relationship. The second sac is filled with 100% pure other component, e.g. oil. The lower ends of the third set of electrodes are left exposed so that they will be immersed in the flow stream when the probe is in an operable position within the flow stream.

As the flow stream flows past the probe, the temperature of both the water and oil in their respective sacs will quickly reach the same temperature as the flow stream due to conduction through the thin-walled sacs. Also, due to the elasticity of the sacs, the pressure on both the water and oil inside the sacs will be substantially equal to that of the flow stream. Therefore, when the electrodes are energized, the set immersed in the water will generate a signal representative of an electrical property (e.g. resistivity) of 100% water; the set of electrodes immersed in the oil generates a signal representative of the resistivity measurement of 100% oil; and the exposed set of electrodes generates a signal representative of the resistivity of the actual flow stream being monitored.

These three signals are fed to a processing unit, e.g. a properly programmed general purpose digital computer, wherein a scale is established having the 100% water signal as one reference limit and the 100% oil signal as the other reference limit. The signal from the flow stream is then related to this scale to determine the concentrations of water and oil in the flow stream at that specific instant in time.

During a monitoring operation, the measurement step described above is continuously repeated at extremely rapid intervals and the results of each step is cumulated and averaged within the process unit so that upon completion of the operation, a read out is provided of the average concentration of each of the two components present in the flow stream during the entire monitoring operation. It can be seen that, since any change in temperature and/or pressure of the flow stream affects each of the signals equally, the resulting relationship between the three signals remains the same and, hence, the accuracy of the final measurements are unaffected by any such changes in the flow stream during a monitoring operation.

BRIEF DESCRIPTION OF THE DRAWINGS

The actual construction, operation, and the apparent advantages of the present invention will be better understood by referring to the drawings in which like numerals identify like parts and in which:

FIG. 1 is a schematic view of a flow monitoring system which incorporates the present invention;

FIG. 2 is a perspective view, partly in section, of the probe of the present invention;

FIG. 3 is a sectional view taken along line 3—3 of FIG. 2, and;

FIG. 4 is a representative view of circuitry used in the present invention.

DESCRIPTION OF THE PREFERRED EMBODIMENTS

Referring more particularly to the drawings, FIG. 1 discloses a multi-component flow stream monitoring system utilizing the present invention. A two-component flow stream, e.g. a mixture of basic sediment and water (BS&W) and oil from a production well, is flowed through conduit 10 and through flow meter 11 which measures the total volume of flow. The stream then flows past probe 12 which is used to measure the concentration of a particular component, e.g. water, in the flow stream.

Referring now to FIGS. 2 and 3, probe 12, as illustrated, is comprised of a housing 15 having a threaded portion 16 adapted to mate with a threaded opening 17 (FIG. 1) in conduit 10. Three substantially identical sensor supports A, B, and C are affixed to housing 15 and extend downward therefrom. Positioned through each support A, B, and C are a pair of electrodes, 18, 19, and 20, respectively. Each pair of electrodes extend completely and by a precise amount through its respective support and are exposed at their lower ends below said support. The upper ends of each electrode terminate within protective shell 15a of housing 15.

Housing 15 and supports A, B, and C are all constructed of a nonconductive material, e.g. polyvinyl chloride, and are preferably molded as a unit with electrodes 18, 19, and 20 in place. However, it should be recognized that other assembly techniques may be used without departing from the present invention. Open passages 21, 22, 14 (FIG. 3) are provided through supports A, B, C respectively, and terminate within shell 15a for a purpose to be described below.

A circumferential groove 25 is preferably formed on at least supports A and B near their lower ends. Individual ballon-like sacs 26, 27 made of a thin-walled, elastic material, e.g. rubber, are positioned over the lower ends of supports A and B, respectively, and are held in place by snap ring 28 or the like. If needed, a skeletal frame-like structure (not shown) made of non-conductive material, e.g. polyvinyl chloride, which may resemble a slotted thimble or the like may be positioned within sacs 26, 27 to prevent collapse, tearing, or major deformation of the respective sac. For the sake of clarity, only support A and sac 26 have been shown in its entirety in FIG. 2; support B being shown as broken away. When sacs 26, 27 are in place, they completely enclose electrodes 18 and 19, respectively, in a fluid-tight relationship. The upper ends of each set of electrodes 18, 19, 20 are adapted to be connected to a set of electrical lead lines 18a, 19a, 20a, respectively, (FIG. 1) which electrically couple probe 12 to processing unit 30, which will be described in more detail below. With the structure of probe 12 now having been fully described, the operation of probe 12 and processing unit 30 will be set forth.

A sample of the flow stream to be monitored is taken and the components are separated. For example, a quantity of a particular lease production stream of oil and BS&W is separated into substantially "pure" lease oil and "pure" lease BS&W components by settling, centrifuging, or the like. Sac 26 on support A is completely filled at atmospheric pressure through passage 21 with the pure lease oil component so that the lower exposed ends of electrodes 18 are completely immersed in the pure lease oil component. Likewise, sac 27 on support A is completely filled through passage 22 with the pure lease BS&W (i.e. water) component so that the lower exposed ends of electrodes 19 are completely submerged in the pure lease water component. The upper ends of passages 21, 22 are then sealed with threaded plugs, friction stoppers, or the like. Passage 14 in support C is also closed off but preferably with a valve (not shown) which, during operations, can be intermittently opened for drawing a sample of the mixture being measured at a specific time for analysis purposes. Probe 12 is assembled into conduit 10 and leads 18a, 19a, and 20a are attached to multi-plexer 31 in processing unit 30.

The oil-BS&W stream flows through flow meter 11 (e.g. 2"–3" positive displacement flowmeter with magnetic pulse pickup, such as Barton Model 380, ITT Barton, City of Industry, Calif.) which measures the total flow of the stream. The physical location of this flowmeter upstream from the probe assists turbulence and thorough fluid mix at the probe. The output of meter 11 is transmitted as pulses through line 35 to counter 33 which in turn is connected into computer 34 of processing unit 30. The oil-BS&W stream flows from meter 11 past probe 12 in conduit 10. Electrodes 18, 19, and 20, are energized and all measure an electrical property (e.g. resistance) of the liquid in which the respective electrodes are immersed and generate respective signals representative of said measurements. That is, electrodes 18, being immersed in pure lease oil, will provide a signal representative of the resistivity measurement of pure lease BS&W; and electrodes 20, being immersed in the flow stream, will provide a signal representative of the resistivity measurement of the actual flow stream which is in contact with probe 12 at that time.

Each of these resistivity signals is transmitted to a terminal (unnumbered) in multiplexer 31 through its respective lead, 18a, 19a, 20a. As understood in the art, multiplexer 31 feeds each signal, in its proper sequence, to an analog to digital converter (ADC) 32 which, in turn, feeds the respective converted digital signal into computer 34. Computer 34, of course, can be a hard-wired apparatus or preferably can be any properly programmed general purpose digital computer. Due to the simplicity of the present invention, a relatively inexpensive "home" computer, e.g. TRS 80 manufactured by Tandy Corp., Ft. Worth, Tex. or "PET" microcomputer, manufactured by Commodore Business Machines, Inc., Santa Clara, Calif., is preferably used to substantially hold down costs in most applications unless a larger unit used elsewhere in a process can "time-share" this function.

Computer 34 is programmed to accept the signal from electrodes 18 and set the value of this signal as being representative of a liquid comprised of 100% lease BS&W. The value of the signal from electrodes 19 is set within computer 34 as being representative of a liquid comprised of 100% lease oil. Computer 34 then subtracts the two signals to calculate a difference therebetween and establishes a scale wherein the resulting difference is spread over a 0–100% range. The signal from electrodes 20 (i.e. resistivity measurement of actual two-component flow stream) is then related by computer 34 to this scale to determine the actual percentage of BS&W (and hence oil) in the monitored flow stream.

To further clarify the above description, an example of a typical measurement operation will be set forth. For a particular lease oil and lease BS&W at a specific temperature and pressure, the actual resistivity readings from electrodes 18 might be 2000 ohms (i.e. 100% oil) and from electrodes 19 might be 20 ohms (i.e. 100% BS&W). These readings are supplied to computer 34 which subtracts the two and takes the resulting difference (i.e. 1800 ohms) and establishes a scale wherein the 1800 ohms is linearly spread over a 100% spectrum. On this scale, a change of 18 ohms in a particular resistivity reading from electrodes 20 would equal a 1% change in the components' concentrations in the monitored flow stream.

In the instant example, a reading of 38 ohms from electrodes 20 would indicate a liquid having 1% oil present in 99% BS&W. Again, it is pointed out that the actual resistivity values given above are by way of example only and actual readings in each practical operation will vary widely depending upon individual probe construction, e.g. electrode spacing, actual field conditions, etc.

Presently known instruments which measure an electrical property of a flow stream to determine the concentration of a component therein are all sensitive to changes in the temperature and/or pressure of the flow stream during measurement. This requires recalibration of these instruments at frequent intervals to reflect the changes in temperature and pressure of the flow stream being monitored to thereby insure accurate measurement of the components when substantial changes occur in the flow stream. The present invention, as will be explained below, is self adjusting to automatically compensate for any changes in both the temperature and pressure of the flow stream substantially instantaneously as they occur.

Although both electrodes 18 and 19 are isolated from direct liquid contact with flow stream by the liquid-filled sacs 26, 27, respectively, both are directly subject to the pressure and temperature of the flow stream. That is, both the oil and the water which fill sacs 26, 27, respectively, will quickly equal the temperature of the flow stream due to heat conduction through the thin-walled sac material. Further, due to the elasticity of sacs 26, 27, the actual pressure of the flow stream will be applied directly to the liquids in the sacs thereby equalizing the pressures inside and outside each sac. Therefore, any changes in temperature and/or pressure of the flow stream during a monitoring operation will result in substantially the same change on all three pairs of sensor electrodes. The simultaneous and equal pressure and temperature changes on each sensor effectively cancels any effects that such changes may have on the actual flow stream measurement.

Again, to further clarify the above description, a change in pressure and/or temperature of the flow stream will change the actual resistivity measurements from each of the three sensors. However, since these changes will inherently be of the same magnitude on all three sensors, the actual relationship between all of the resistivity measurements remains unchanged. By programming computer 34 to (1) record the instantaneous measurement from electrodes 18 and set this value equal to 100% oil, (2) record the instantaneous measurement from electrodes 19 and set this value equal to 100% water, (3) substract the two measurements to get the instantaneous difference, (4) record the instantaneous measurement from electrodes 20 and relate it to the instantaneous difference, the concentration of water, and hence oil, can be calculated and recorded by computer for each series of resistivity readings.

Individual sets of the three measurements (i.e. 100% water, 100% oil, and actual flow stream) are made at rapid intervals (e.g. at rates of from 1 to 200 sets of measurements per second) and each set, which represents the concentration of the flow stream at the time said set of measurements is made, is calculated and stored in processing unit 30. These sets of measurements are then cumulated and averaged within computer 34 so upon completion of a monitoring operation, the average concentration of water, and hence average concentration of oil (i.e. 100%-concentration of water) in the monitored flow stream is available as a final readout from computer 34. Alternatively, these final concentrations of water and oil can be combined within computer 34 with the volume readings from meter 11 (FIG. 1) to calculate the actual amounts of oil and water that were flowed through conduit 10 during the monitoring period.

Although resistivity has been used as the electrical property being measured in the above description, other electrical properties of liquids can be used as well. Conductivity which is the reciprocal of resistivity can be used by properly programming the processing unit and modifying the electrodes energizing circuit. Capacitance can also be used although it is the least preferable as the other two mentioned properties since additional electronics are required which must be mounted as close to the electrodes (e.g. on probe 15) as possible to avoid long lead lines with consequential extra capacitance. Where capacitance is the measured property, a bridge circuit 50 (FIG. 4) would need to be provided for each set of electrodes 18, 19, 20, respectively, with the electrodes, e.g. 18, and leads 18a being coupled into bridge 50 as shown. As understood in the art, additional circuitry for frequency generation would also be required.

What is claimed is:

1. A method for measuring the concentration of a particular component in a two-component liquid mixture, said method comprising:
    measuring an electrical property of said particular component at the pressure and temperature of said two-component mixture;
    generating a first signal representative of said measured electrical property of said particular component;
    concomitantly measuring the same electrical property of the other component of said two-component liquid mixture at the pressure and temperature of said two-component mixture;
    generating a second signal representative of said measured electrical property of said other component;
    concomitantly measuring the same electrical property of said two-component mixture;
    generating a third signal representative of said measured electrical property of said two-component mixture;
    establishing a scale having said first signal representative of liquid having 100% of said particular component and having said second signal representative of a liquid having 100% of said other component; and
    determining said concentration of said particular component in said two-component liquid mixture by the relationship of said third signal on said scale.

2. The method of claim 1 wherein said electrical property is resistance.

3. The method of claim 1 wherein said electrical property is conductance.

4. The method of claim 1 wherein said electrical property is capacitance.

5. A method of measuring the concentration of a particular component in a two-component liquid flow stream, said method comprising:
generating a first signal representative of an electrical property of said particular component at the pressure and temperature of said flow stream;
generating a second signal representative of the same electrical property of the other component of said two-component flow stream at the pressure and temperature of said flow stream;
generating a third signal representative of the same electrical property of said two-component flow stream;
establishing a scale having said first signal representative of a liquid having 100% of said particular component and having said second signal representative of a liquid having 100% of said other component; and
relating said third signal to said scale to determine said concentration of said particular component in said two-component flow stream.

6. The method of claim 5 wherein:
said first signal is generated by a first sensor immersed in said particular component, said first sensor and immersing particular component being positioned into said flow stream whereby said immersing particular component is directly responsive to the temperature and pressure of said flow stream;
said second signal is generated by a second sensor immersed in said other component, said second sensor and immersing other component being positioned into said flow stream whereby said immersing other component is directly responsive to the temperature and pressure of said flow stream; and
said third signal is generated by a third sensor which is positioned into the flow stream whereby said third sensor is in direct fluid contact with said flow stream.

7. The method of claim 6 wherein said electrical property is resistance.

8. The method of claim 6 wherein said electrical property is conductance.

9. The method of claim 6 wherein said electrical property is capacitance.

10. Apparatus for use in measuring the concentration of a particular component in a two-component liquid mixture, said apparatus comprising:
a first means responsive to the temperature and pressure of said two-component liquid mixture for generating a first signal representative of an electrical property of said particular component;
a second means responsive to the temperature and pressure of said two-component liquid mixture for generating a second signal representative of the same electrical property of the other component of said two-component liquid mixture; and
a third means responsive to the temperature and pressure of said two-component liquid mixture for generating a third signal representative of the same electrical property of said two-component liquid mixture.

11. The apparatus of claim 10 wherein said electrical property is resistance.

12. The apparatus of claim 10 wherein said electrical property is conductance.

13. The apparatus of claim 10 wherein said electrical property is capacitance.

14. Apparatus for use in measuring the concentration of a particular component in a two-component liquid mixture, said apparatus comprising:
a housing;
a first set of electrodes extending through said housing and having their lower ends adapted to be positioned within said two-component liquid mixture when said housing is in an operable position, said first set of electrodes adapted to generate a signal representative of an electrical property of a liquid in contact with said first set of electrodes;
first means for enclosing said lower end of said first set of electrodes in a fluid tight relationship, said first means being responsive to the temperature and pressure of said two-component liquid mixture when said housing is in an operable position and adapted to be filled with said particular component whereby said lower end of said first set of electrodes will be totally immersed in said particular component when said first means is filled;
a second set of electrodes extending through said housing and having their lower ends adapted to be positioned within said two-component liquid mixture when said housing is in an operable position, said second set of electrodes adapted to generate a signal representative of said electrical property of a liquid in contact with said second set of electrodes;
second means for enclosing said lower end of said second set of electrodes in a fluid tight relationship, said second means being responsive to the temperature and pressure of said two-component liquid mixture when said housing is in an operable position and adapted to be filled with the other component of said two-component liquid mixture whereby said lower end of said second set of electrodes will be totally immersed in said other component when said second means is filled; and
a third set of electrodes extending through said housing and having their lower ends adapted to be positioned within and in direct contact with said two-component liquid mixture when said housing is in an operable position, said third set of electrodes adapted to generate a signal representative of said electrical property of said two-component liquid mixture.

15. The apparatus of claim 14 wherein said first means comprises:
a flexible sac; and
means for attaching said flexible sac in a fluid tight relationship around said lower ends of said first set of electrodes;
and wherein said second means comprises:
a flexible sac; and
means for attaching said flexible sac in a fluid tight relationship around said lower ends of said second set of electrodes.

16. Apparatus for use in measuring the concentration of a particular component in a two-component liquid flow stream, said apparatus comprising:
a housing;
a first sensor support on said housing;
a first set of electrodes extending through said housing and said first sensor support, the lower ends of said first electrodes terminating below said first sensor support whereby said lower ends are exposed below said first sensor support, the upper ends of said first electrodes adapted to be electrically coupled to a processing unit;

a first elastic sac secured to said first sensor support and enclosing said lower ends of said first set of electrodes in a fluid tight relationship;

a passage means through said first sensor support for filling said first elastic sac with a liquid;

a second sensor support on said housing;

a second set of electrodes extending through said housing and said second sensor support, the lower ends of said second electrodes terminating below said second sensor support whereby said lower ends are exposed below said second sensor support, the upper ends of said second electrodes adapted to be connected to a processing unit;

a second elastic sac secured to said second sensor support and enclosing said lower ends of said second set of electrodes in a fluid tight relationship;

a passage means through said second sensor support for filling said second elastic sac with a liquid; and a third sensor support on said housing;

a third set of electrodes extending through said housing and said third sensor support, the lower ends of said third electrodes terminating below said third sensor support whereby said lower ends are exposed below said third sensor support, the upper ends of said third electrodes adapted to be electrically coupled to a processing unit.

17. The apparatus of claims 14 or 16 including:

processing means for processing said first, second, and third signals to determine the percentage of said particular component in said two-component liquid mixture;

means for transmitting said signal from said first set of electrodes to said processing means;

means for transmitting said signal from said second set of electrodes to said processing means; and means for transmitting said signal from said third set of electrodes to said processing means.

18. The apparatus of claim 16 including:

a passage means through said third sensor support for withdrawing a sample of said two-component liquid flow stream when said apparatus is in an operable position.

* * * * *